United States Patent [19]

Falb et al.

[11] 4,318,709

[45] Mar. 9, 1982

[54] TEST MEANS, TEST DEVICE AND METHOD FOR DETERMINING THE IONIC STRENGTH OR SPECIFIC GRAVITY OF A LIQUID SAMPLE

[75] Inventors: Richard D. Falb, Bristol, Ind.; Sisto N. Stiso, San Jose, Calif.; Yung-Chyung Wang, Kaohsiung, Taiwan; William I. White, Elkhart; Rodric H. White-Stevens, Howe, both of Ind.

[73] Assignee: Miles Laboratories, Inc., Elkhart, Ind.

[21] Appl. No.: 168,466

[22] Filed: Jul. 10, 1980

Related U.S. Application Data

[63] Continuation-in-part of Ser. No. 958,630, Nov. 8, 1979, abandoned.

[51] Int. Cl.$^3$ .................. G01N 9/36; G01N 31/04; G01N 31/22; G01N 33/52
[52] U.S. Cl. .................. 23/230 R; 23/230 B; 73/32 R; 252/408; 422/56; 422/57; 525/369
[58] Field of Search .................. 23/230 B, 230 R; 422/56, 57

[56] References Cited

U.S. PATENT DOCUMENTS

| | | | |
|---|---|---|---|
| 2,607,762 | 8/1952 | Bowen | 525/369 |
| 2,757,153 | 7/1956 | Bowen | 525/369 X |
| 3,449,080 | 6/1969 | Edwards | 422/56 X |
| 4,108,727 | 8/1978 | Stiso | 23/230 B X |
| 4,287,153 | 9/1981 | Towsend | 422/56 |

FOREIGN PATENT DOCUMENTS

46-4905  2/1971  Japan.

*Primary Examiner*—Sidney Marantz
*Attorney, Agent, or Firm*—Edward H. Gorman, Jr.

[57] ABSTRACT

A test means for determining the ionic strength or specific gravity of an aqueous test sample, the test means comprising a weakly acidic or weakly basic polyelectrolyte which is at least partially neutralized, and an indicator means capable of producing a detectable response to ion exchange between the polyelectrolyte and the sample. The test device comprises a carrier matrix incorporated with the test means, and the method for its use comprises contacting an aqueous test sample with the device and observing a detectable response.

25 Claims, 8 Drawing Figures

TEST MEANS, TEST DEVICE AND METHOD FOR DETERMINING THE IONIC STRENGTH OR SPECIFIC GRAVITY OF A LIQUID SAMPLE

CROSS-REFERENCES TO RELATED APPLICATIONS

The present application is a Continuation-in-part of United States Patent Application Ser. No. 958,630, filed Nov. 8, 1979, now abandoned.

BACKGROUND OF THE INVENTION

1. Field of the Invention

The present invention relates to the determination of the ionic strength or specific gravity of a test sample. More particularly it relates to a test means, test device and method for determining the ionic strength or specific gravity of an aqueous test sample.

2. Description of the Prior Art

The determination of the specific gravity of a liquid has application in numerous arts. Thus, such unrelated disciplines as brewing, urinalysis, water purification, preparation of drinking water aboard a ship at sea, etc., all involve the measurement of specific gravity. Needless to say, a quick, facile method for determining this property would greatly enhance the state of many scientific arts, including any technology where rapid, accurate determination of specific gravity would be beneficial. Thus, for example, if a medical laboratory technician could accurately measure the specific gravity of a urine sample in a matter of seconds, not only would the rapid results aid the physician in diagnosis, but also laboratory efficiency would increase to a degree where many more analyses could be performed than were heretofore possible.

Although the present invention lends itself to a vast range of applications, for purposes of clarity this discussion will be couched largely in terms of the determination of the ionic strength or specific gravity of urine. Applications to other disciplines will become apparent from an understanding of how this invention relates to urinalysis.

The determination of urine specific gravity is of considerable value in the understanding and clinical management of electrolyte disturbances. Hence, complete urinalysis should, and usually does, include a specific gravity determination. Generally, such a determination would include the measurement of specific gravity directly with a suitable device, but equally useful is the measurement of some related property, such as osmolality or ionic strength, which can then be referred back to corresponding specific gravity values.

Specific gravity is a dimensionless term and relates, in the case of a solution, to the ratio of the weight of a certain volume of the solution to that of an equal volume of water at the same temperature. For solutions such as urine, the specific gravity is a function of the number, density, ionic charge, and weight of the various species of dissolved solutes.

Prior art methods for determining specific gravity utilize hydrometers, urinometers, pycnometers, gravimeters and the like. Although these prior art procedures are satisfactorily sensitive in most cases, they all involve fragile, bulky instruments which must be constantly cleaned, maintained, and calibrated in order to continuously assure their reliability. In addition, there are many inconveniences associated with the mechanics of using these instruments. There may be a difficulty in reading the miniscus. Froth or bubbles on the liquid surface may interfere with the reading. There is a tendency for urinometers to adhere to the sides of the vessel containing the liquid sample. In the case of urine, the sample quantity is frequently inadequate for accommodating one of the aforementioned devices.

A recent breakthrough in which all of the above disadvantages have been virtually eliminated, and which affords rapid osmolality (ergo, specific gravity) determination, is disclosed in U.S. Pat. No. 4,015,462, filed by Greyson et al., on Jan. 8, 1976 and assigned to the present assignee. This patent describes an invention in which a carrier matrix is incorporated with osmotically fragile microcapsules, the walls of which are composed of a semi-permeable membrane material. Encapsulated inside the walls is a solution containing a coloring substance. When the capsules are in contact with a solution having a lower osmolality than that within the capsules, an osmotic gradient occurs across the capsule walls in the direction of the lower osmolality, thereby increasing the hydrostatic pressure within the capsules, thus causing them to swell and, ultimately, to rupture, releasing their colored contents. The amount of color formed from this phenomenon is a function of the specific gravity of the solution.

It can be seen from the foregoing that besides the numerous devices which measure specific gravity directly, it is also possible to measure specific gravity using an indirect means such as the osmolality of a solution. Yet another way of estimating specific gravity without measuring it directly involves a determination which is proportional to the ionic strength of a solution. Such an approach is utilized by the present invention. It is well known that the specific gravity of an aqueous system is greatly affected by the presence of charged species. Thus, in the case of ionic solutions, it is possible to closely approximate the specific gravity of the respective solutions via measurements proportional to their ionic strengths and referring those measurements to a precalibrated reference system.

The term "ionic strength" refers to the mathematical relationship between the number of different kinds of ionic species in a particular solution and their respective charges. Thus, ionic strength $\mu$ is represented mathematically by the formula $$\mu = \tfrac{1}{2} \sum_i C_i z_i^2$$

in which c is the molal concentration of a particular ionic species and z the absolute value of its charge. The sum $\Sigma$ is taken over all the different kinds of ions in solution.

U.S. Pat. No. 3,449,080 discusses measuring dissolved sodium or chloride ions. This reference is directed to a test device for determining the concenrations of these ions in body sweat. Briefly, there is disclosed in this patent the use of ion exchange resins together with a pH indicator. Using this device, the presence of sodium or chloride ions is said to be determined through a color change in the ion exchange resin caused by the pH indicator. Whereas this reference purports to disclose a way of measuring ionic strength, it was found by the present inventors that such teachings, as set forth in the examples, were inapplicable to the measurement of specific gravity.

Both the osmolality approach and the ionic strength approach to indirectly determining specific gravity could conceivably be affected insofar as accuracy is concerned by the presence of nonionic species. Accordingly, U.S. Patent Application Ser. No. 716,962, filed Aug. 23, 1976, U.S. Pat. No. 4,108,727, is directed to a method for removing this potential source of inaccuracy, and discloses a device in which the specific gravity-sensitive system contains an ionizing agent capable of converting the nonionic solute to ionized species.

To summarize the present state-of-the-art as it might pertain to the present invention, many methods are known for the measurement of specific gravity, both direct and indirect. Direct measurement includes utilizing devices which are fragile, bulky and inexpensive, and which must be constantly cleaned, maintained and calibrated. Of the indirect methods, the measurement of the colligative solution property known as osmolality can provide an accurate correlation to specific gravity. The present invention utilizes a different perspective, the relationship between specific gravity and the ionic strength of a solution, and provides a device, composition and method for taking advantage of this relationship. U.S. Pat. No. 3,449,080 describes a method of gauging the concentration of sodium and/or chloride ions in body sweat. This reference utilizes the affinity of weakly acidic or weakly basic ion exchange resins for the unknown ions, and the color changing capacity of known pH indicators. None of the prior art known to the present inventors at the time of filing of the instant application teaches or suggests the invention presently disclosed and claimed.

SUMMARY OF THE INVENTION

Briefly, the present invention relates to a test means, device, the method for determining the specific gravity of an aqueous test sample. The test means comprises a weakly acidic or weakly basic polyelectrolyte polymer, which has been at least partially neutralized, and an indicator substance capable of producing a detectable response to ion exchange between the polyelectrolyte and the test sample. The device of the present invention comprises a carrier matrix incorporated with the test means. The method of the present invention comprises contacting a test sample with the device or test means and observing a detectable response such as a change in color, pH or enzyme activity.

BRIEF DESCRIPTION OF THE DRAWINGS

FIGS. 1–8 are graphic portrayals of (a) the responses of three polyelectrolytes to test samples having verying specific gravities, and (b) the titration of partial neutralization of these polymers. Thus

DETAILED DESCRIPTION OF THE INVENTION

The presently claimed test means comprises, as one ingredient, a weakly acidic or weakly basic polyelectrolyte. Numerous examples of such polymers are known in the art, their common characteristics centering about the degree of dissociation of the ionic pendant groups when the polymer is subjected to an aqueous environment. Most polyelectolytes are soluble or partially soluble in water, and are readily ionizable, depending on the ionic nature of (a) the aqueous system and (b) the ionizable species on the polymer chain.

Thus a polyelectrolyte is branded weakly or strongly ac acidic or basic depending on its ionic behavior. Generally, a polyelectrolyte which nearly completely ionizes when contacted with water, such as poly(vinylsulfuric acid) and poly(styrene sulfonic acid), are considered strong polyelectrolytes. Weak polyelectrolytes on the other hand, contain weakly acidic or basic ionizable groups. The charge density along the molecular chain of these polymers can be varied by varying the degree of neutralization. Examples of weakly acidic or weakly basic polyelectrolytes which find particular applicability to the present invention are poly(arcylic acid), poly(-maleic acid), maleic acid/methylvinyl ether copolymer, poly(methacrylic acid), styrene-maleic acid copolymer, poly(4-vinylpyridine), and others.

The composition and test means of the present invention includes weakly basic and weakly acidic polyelectrolytes, but more particularly it includes those which have been partially neutralized. At least some of the functional groups of the polymer, be they weakly acidic (e.g., COOH) or weakly basic, are first partially titrated with a base or acid, respectively, prior to incorporating the polyelectrolyte into the test composition. Typically, aqueous solutions of titrant are employed, and basic titrants include solutions of NaOH, KOH, $Na_2CO_3$, poly(ethyleneimine), tris(hydroxymethylamine) methane and others known to chemists reasonably skilled in the art. Surprisingly, such partial titration or neutralization has been found to be necessary in order to enable significant differentiation between specific gravity levels in test solutions.

Preferably, the polymer is neutralized to at least about 50%, i.e., at least about half of the ionizable groups are neutralized. An ideal neutralization range, and that presently found most preferred in the present invention, is from about 75 to about 95% neutralization, 90% having thus far been found to be optimum in providing the largest separation in pH change or other detectable response with respect to specific gravity or ionic strength.

The polyelectrolyte selected for use in the present invention must, as stated supra, be partially neutralized. This is accomplished by titration of the polymer with suitable acid or base as desired, or by any other means which achieves the desired result of partial neutralization. Thus, FIG. 1 constitutes the titration curve of Gantrez ® S-97, a maleic anhydride/methylvinylether copolymer marketed by General Aniline and Film Corporation, with sodium hydroxide in aqueous solution. FIG. 2 shows similar data for poly(acrylic acid), and FIG. 3 poly(vinylamine).

Another element of the present invention is an indicator means. It can take on such diverse forms as a pH indicator compound, an enzymatic system whose function is responsive to subtle pH changes, a pH meter, and pH-sensitive antigen/antibody systems. Thus, known pH-sensitive chromogenic reagent compounds can be employed, and these can provide a change in or appearance of color, observable by the person performing the measurement, which is indicative of the ionic strength of specific gravity of the system being tested. If a chromogen is used, a reference color system can be established beforehand, so that a quick visual comparison of the composition and the reference system provides the sought after results. Examples of chromogens suitable for use in the present invention are bromothymol blue, alizarin, bromcresol purple, phenol red and neutral red; bromothymol blue having been found to be especially suitable.

Alternatively, the indicator means can take the form of a pH meter, whereby small changes in pH can be monitored directly, without resorting to visual observation of color change. One particularly suitable approach is to use the pH meter in conjunction with a surface pH electrode. The pH meter response can then be observed over various ionic strength values and a reference system can be established, a particular change in pH corresponding to a particular test sample ionic strength.

Yet another ramification of the indicator means is a pH-sensitive enzyme-based system, whereby subtle changes in pH caused by the polyelectrolyte/ionic strength interaction can trigger the onset of enzymatic activity, or which can change kinetic reaction parameters such as the $K_M$ for a particular enzymatic reaction. Thus an enzymatic system capable of providing a detectable response can be triggered to produce that response in accordance with the specific gravity or ionic strength of a test sample. For example, the enzyme chymotrypsin is known to be sensitive to pH in acting on the substrate p-nitrophenyl acetate to yield p-nitrophenol. Thus the reaction rate dramatically increases from pH 6 to 8, and the appearance of the yellow p-nitrophenol is markedly enhanced by pH increases in that range.

Similarly, an antigen-labeled substrate can be employed. The pH dependence of antigen/antibody reactions is well known, and the indicator means of the present invention can include such a labeled substrate and the antibody for the label. Change in pH can be measured by change in substrate available for a corresponding enzymatic reaction.

The present invention includes a device in which a carrier matrix is incorporated with the presently disclosed composition or test means to provide a tool for obtaining rapid, reliable estimations of solution specific gravities. The carrier matrix is usually, but not necessarily, a porous substance such as filter paper. Other art-recognized forms of carrier matrix materials are felt, porous ceramic strips, and woven or matted glass fibers (U.S. Pat. No. 3,846,247). Also suggested are the use of wood, cloth, sponge material and argillaceous substances (U.S. Pat. No. 3,552,928). All such carrier matrix materials are feasible for use in the present invention, as are others. It has been found that filter paper is especially suitable.

In a preferred embodiment, filter paper is wetted with a solution of suspension of a partially neutralized polyelectrolyte in water or other suitable vehicle easily determinable by routine laboratory experiments and then dried. The polyelectrolyte-bearing filter paper is subsequently incorporated with the desired indicator means. Typically, the paper is wetted with a solution of a pH-sensitive chromogenic indicator (such as bromothymol blue) in methanol or other suitable solvent such as ethanol, N,N-dimethylformamide, dimethylsulfoxide, and subsequently dried. Alternatively, a one-dip method can be used whereby the polyelectrolyte and indicator means are simultaneously present in the initial solution or suspension.

The dried, reagent-bearing carrier matrix can be mounted on a backing material if desired. The test device, in a preferred embodiment, thus comprises a filter paper carrier matrix, incorporated with a partially neutralized polyelectrolyte and indicator means as described supra, the matrix being affixed to one side to an elongated piece of transparent polystyrene film. The matrix is secured to one end of the film by any suitable means, such as double faced adhesive tape (Double Stick ® available from 3M Company), the other end of the polystyrene film serving as a handle. In use, such a device is held by the free end of the polystyrene film backing material and the matrix end is immersed into the test sample (e.g., urine) and quickly removed. Any color formation or other detectable response is observed after a predetermined time and compared with a reference standard corresponding to responses to known solution ionic strengths or specific gravities.

The particular reference standard employed depends on whether the test means is used by itself or incorporated with a carrier matrix, as well as on the particular indicator means. Thus if the partially neutralized polyelectrolyte is added directly to the test sample, and the indicator means is a pH meter, a reference standard can be devised by adding a standard weight of polyelectrolyte to a standard volume of a solution of known ionic strength. The pH change before and after polyelectrolyte addition is recorded using the pH meter. This procedure is followed for a series of solutions having varied known ionic strengths. To determine the ionic strength of an unknown test sample, the same procedure is followed by the pH change compared with those for the known solutions.

Where a test device comprising a carrier matrix containing partially neutralized polyelectrolyte and a chromogen is employed, a reference standard can comprise a series of color blocks depicting the color developed by the carrier matrix after a predetermined time in response to solutions of known ionic strengths. When testing on unknown sample, the carrier matrix of a test device is immersed in the sample, removed, and observed for the appearance of or change in color after the predetermined time. Any color response is then compared with the reference standard color blocks to ascertain the ionic strength or specific gravity of the sample.

The following Examples are provided to further teach how to make and use the present invention. Thus, preferred embodiments are described and analyzed. The Examples are meant to be illustrative only, and are in no way intended as limiting the scope of the invention described and claimed herein.

A. THE TEST MEANS

Example I—Partial Neutralization of Maleic Anhydride/Methylvinylether Copolymer This experiment was performed to study the partial neutralization of polyelectrolyte (Gantrez S-97 marketed by General Aniline and Film Corporation), and its effect on a composition for measuring solution specific gravity.

A modular automatic titrator was assembled for the titration of various polyelectrolytes for study pertinent to the present invention. The titrator consisted of an automatic pipetter, Model No. 25000, from Micromedic Systems, Inc. This instrument is capable of dispensing a constant volume of titrant per unit time into the polymer solution to be titrated. The rate of addition of titrant (ergo, the rate of polyelectrolyte neutralization), was controlled through the selection of pipette volume, the fraction of pipette volume dispensed, and the concentration of titrant. Changes in pH during titration were detected using a standard pH electrode and an Orion Model 701 digital pH meter. The output of the pH meter was fed into a Hewlett-Packard Model 17500A ten inch strip chart recorder, the scale of which had been calibrated such that one inch corresponded to a change of one pH unit. Hence, the recorder provided a continuous monitor of pH changes with respect to time (ergo with respect to volume of titrant added).

This apparatus was used to titrate and observe the effects of partial neutralization on Gantrez S-97, a weakly acidic polyelectrolyte. A solution of Gantrez was prepared comprising 20 grams of the polyelectrolyte per liter of deionized water. Three 100 milliliter (ml) aliquots of this solution were placed in 250 ml beakers. One aliquot was made 0.1 N and another 1.0 N with NaCl. No salt was added to the remaining aliquot. By titrating each of these polyelectrolyte solutions with 1.0 N NaOH in a 50 ml pipette at a rate of 9.0 ml. titrant per hour, and recording pH change versus volume of titrant, it was possible to study the titration characteristics of Gantrez, as well as the effects of partial neutralization on its ability to differentiate varying ionic strengths.

Figure 1:
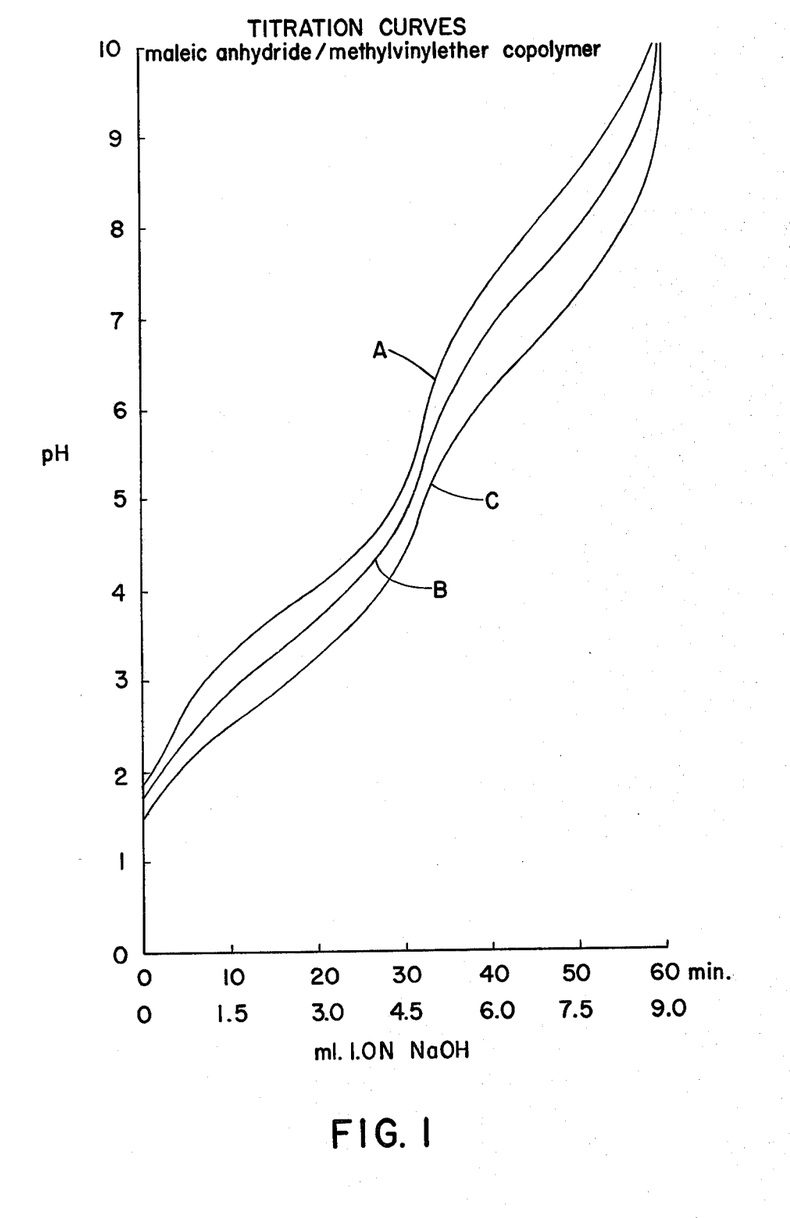
FIGS. 1, 2 and 3 are titration curves for a copolymer of methyl vinyl ether and maleic anhydride, poly(acrylic acid), and poly(-vinylamine) respectively.
Figure 2:
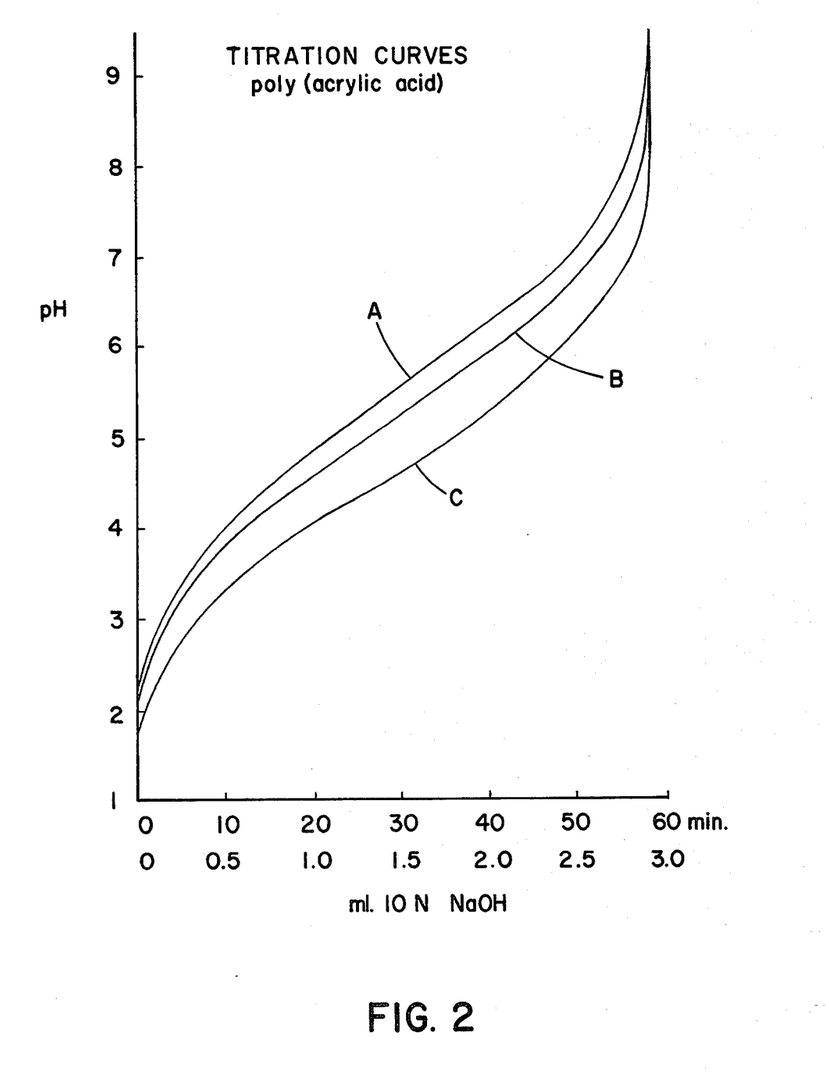

The titration data obtained in this experiment is plotted graphically in FIG. 1. Curve A represents the titration of the polyelectrolyte solution to which no salt was added, curve B represents titration of the polyelectrolyte solution made 0.1 N in NaCl, and curve C represents the titration of the polyelectrolyte solution containing NaCl at 1.0 N concentration. The clear separation which occurs between curves A, B and C in FIG. 1 is indicative of the effect of ionic strength on the apparent pH of the polymer. Thus, by observing the degrees of separation between the titration curves, i.e., of pH values for a given amount of titrant, one can estimate maximization with respect to determining different levels of specific gravity. For example, greater separation is observed in the regions between pH 5 and pH 10 than at other stages of polymer neutralization. The curves in FIG. 1 indicate that optimum separation occurs with a degree of polymer neutralization from about 70% to 95% or more (i.e., addition of about 6.0 to 9.0 ml. titrant). Not only is this information useful in gauging the effectiveness of the polymer in aqueous systems, but it also helps towards determining optimum neutralization of the polyelectrolyte for incorporation with a carrier matrix as will be seen in Example IV, infra.

The percent neutralization of a given polyelectrolyte can be calculated from titration data such as that presented graphically in FIG. 1 by curve A (the titration of the polyelectrolyte, here Gantrez S-97, with no added salt). Percent neutralization of the polymer is calculated for a given pH of titrated polymer solution by finding the solution pH on the vertical axis, extending a horizontal line from the vertical axis to curve A, and extending a vertical line from that point on curve A to the horizontal axis (i.e., ml. of 1.0 N NaOH). The volume of titrant (corresponding to the intersection of the vertical line and the horizontal axis) divided by the titrant volume at the end point of titration, multiplied by 100 yields a close approximation of the percent of polyelectrolyte neutralization. Titration end point is indicated by vertical linearity of curve A at the far right, and can be expressed in terms of the volume of titrant added.

Thus, for Gantrez S-97, the end point shown in FIG. 1 is very close to 9.0 (about 8.6) ml of 1.0 N NaOH titrant. Titration of the Gantrez solution in deionized water to a pH of about 7.5 corresponds to a volume of about 6.0 ml titrant. Since the end point is about 8.6 ml of titrant, percent neutralization is calculated by $$\frac{6.0 \text{ ml.} \text{ (titrant)}}{8.6 \text{ ml.} \text{ (titrant at end point)}} \times 100 = 70 \text{ (percent neutralized)}$$

Example II—Partial Neutralization of Poly(acrylic acid)

This experiment was performed to study the partial neutralization of poly(acrylic acid) and the effects of such neutralization on the usefulness of this polyelectrolyte in determining solution specific gravity. The modular automatic titrator, pH meter and electrode described in Example I were employed, as was the procedure.

A solution of the poly(acrylic acid), a weakly acidic polyelectrolyte obtained from Aldrich Chemical Co. (Catalogue No. 19,205-8), was prepared by dissolving 20 grams of polymer in one liter of deionized water. Aliquots of 100 milliliters each of this solution were placed in 250 ml beakers. One of the aliquots was made 0.1 N and another 1.0 N in NaCl. No salt was added to the third aliquot. Each of these solutions was then titrated with 10.0 N NaOH in a 50 ml. pipette at a rate of 3.0 ml. titrant per hour. The results are reported in FIG. 2 in which curve A represents the polyelectrolyte solution containing no salt, curve B the solution made 0.1 N in NaCl, and curve C the solution made 1.0 N in NaCl.

The data depicted by FIG. 2 illustrates that the greatest separation with respect to ionic strength (i.e., between curves A, B and C) occurs from about 50% to about 95% or greater neutralization of the polymer (i.e., addition of about 1.5 to about 3.0 ml. titrant). Thus, for example, where the polymer has been titrated over a 40 minute period (with 2.0 milliliters of 10 N NaOH), one can see marked separation of the resultant pH depending upon the ionic strength of the solution. Curve C which corresponds to 1.0 N NaCl provides a resultant pH value of about 5.25, curve B corresponding to 0.1 N NaCl yields a pH value of about 5.8, and curve A, which corresponds to zero concentration of NaCl, yields a pH value of about 6.25. Thus, the ionic strength or specific gravity of a particular solution can be approximated by using these values and interpolating between them.

Example III—Partial Neutralization of Poly(vinylamine)

This experiment was performed by study the partial neutralization of a weakly basic polyelectrolyte, poly(vinylamine) obtained from Dynapol, Inc., and the effects of such neutralization on the usefulness of this polyelectrolyte in determining specific gravity. The modular automatic titrator, pH meter and electrode described in Example I were employed, as well as the procedure.

A solution of poly(vinylamine) in its hydrochloride salt form (completely neutralized) having a molecular weight of about 60,000 was prepared having a polmer concentration of 20.0 grams per liter of deionized water. Three aliquots of 100 milliliters each of this solution were placed in 250 ml beakers. One of the aliquots was made 0.5 N and another 3.0 N in NaCl. No salt was added to the remaining aliquot. Each of these solutions was then titrated with 1.0 N NaOH using a 50 milliliter pipette at a rate of 9.0 ml titrant per hour. The results are depicted in FIG. 3 in which curve A represents titration of the polyelectrolyte solution to which no salt was added, curve B the solution made 0.5 N in NaCl and curve C titration of the solution made 3.0 N in NaCl.

Figure 3:
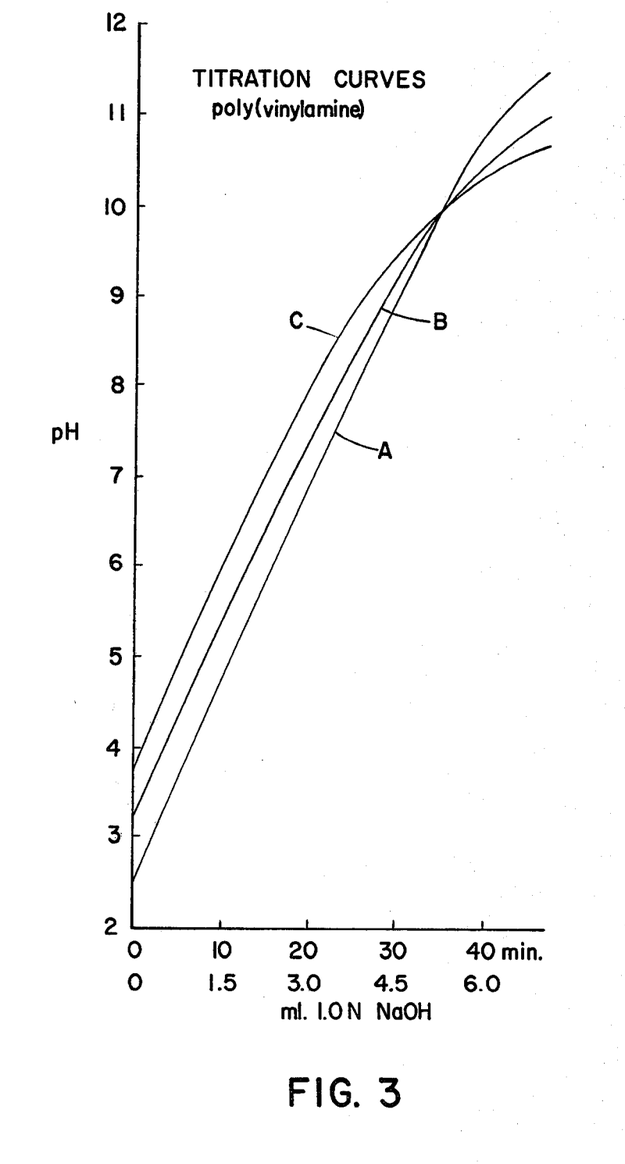

The data in FIG. 3 shows that little response occurs with respect to ionic strength when the polymer is completely in the amine or nonneutralized form (pH 10, 35 minutes), whereas excellent separation occurs at lower degrees of titration, i.e., where neutralization of the polymer is more extensive. Hence, the ability of poly(vinylamine) to differentiate different ionic strength levels varies inversely with the amount of titrant, such that at the onset of the titration (in excess of 95% neutralization) excellent separation is produced, whereas at zero neutralization (addition of about 5.3 ml. titrant), no separation occurs.

B. THE TEST DEVICE

Example IV—Performance of Maleic Anhydride/Methylvinylether Copolymer in a Carrier Matrix A test device sensitive to ionic strength or specific gravity was prepared by incorporating the solution of Gantrez S-97 into filter paper and then drying. Several test devices were prepared in order to study the performance of the polyelectrolyte at various degrees of neutralization. Thus, aliquots of the Gantrez S-97 solution were neutralized to different extents by titration with NaOH. Strips of filter paper obtained from Eaton and Dikeman (No. 204) were respectively immersed in these partially titrated aliquots and subsequently dried. Impregnated dried strips made from each of the aliquots were then respectively dipped into urines having different known specific gravities and into deionized water, and the pH thereof was measured. A pH meter having a flat surface electrode obtained from Markson Science, Inc. (No. 1207 BactiMedia combination pH/reference electrode) was used for these measurements. The values of $\Delta pH$, i.e., the difference in the pH of identical strips dipped respectively into deionized water and urine of known specific gravity, are tabulated below.

| pH of Poly-electrolyte Solution Aliquots | $\Delta$ pH Values Produced by Urines of Indicated Specific Gravities | | |
|---|---|---|---|
| | Sp. Gr. 1.030 | Sp. Gr. 1.015 | Sp. Gr. 1.005 |
| 4.75 | 0.20 | 0.29 | 0.32 |
| 6.0 | 1.04 | 0.91 | 0.54 |
| 7.0 | 1.70 | 1.44 | 0.65 |
| 8.0 | 2.41 | 2.06 | 1.04 |
| 9.25 | 3.24 | 2.29 | 1.09 |
| 9.75 | 3.52 | 2.66 | 1.65 |

Figure 4:
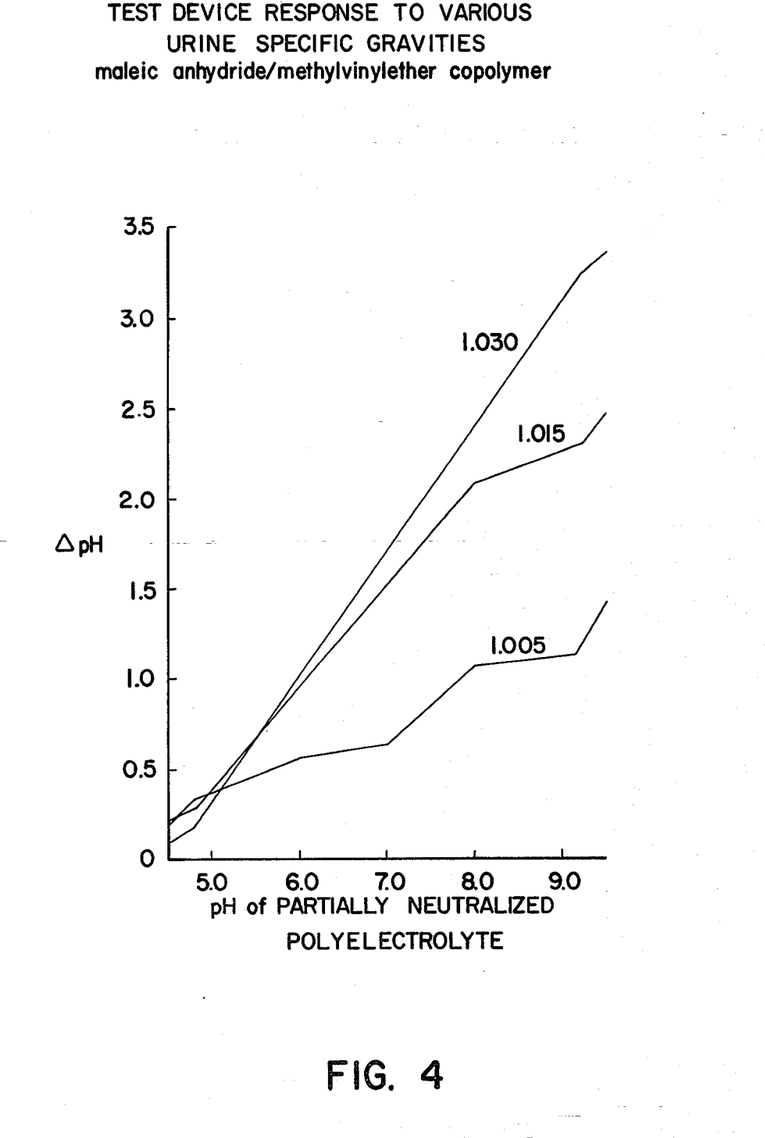
FIGS. 4, 5 and 6 depict the performances of these polyelectrolytes in determining urine specific gravities after varying degrees of partial neutralization of the polymer pendant group.

The data in the above table has been plotted in FIG. 4, wherein the three curves represent values of $\Delta pH$ produced by urines having the indicated specific gravity values when tested with strips made from aliquots of different degrees of neutralization. It can be seen from FIG. 4 that the degree of separation of the curves increases markedly as the degree of neutralization of the polyelectrolyte, i.e., the pH, increases. Thus, the more partial neutralization of the Gantrez polyelectrolyte, the greater the ability to differentiate between specific gravity levels in urine.

Example V—Performance of Poly(acrylic acid) in a Carrier Matrix

The polyelectrolyte employed in Example II (20 grams of poly(acrylic acid) per liter of deionized water) was further studied to observe its behavior in measuring urine specific gravity when incorporated with a carrier matrix.

Test devices were prepared and tested as in Example IV, except that poly(acrylic acid) was substituted for Gantrez S-97. A solution of 20 grams of poly(acrylic acid) per liter of deionized water was prepared. Aliquots of this solution were titrated with 10 N sodium hydroxide until the pH levels stated in the table below were achieved. Strips of filter paper obtained from Eaton and Dikeman (No. 204) were respectively dipped into these aliquots and dried. They were then respectively dipped into urines of different known specific gravity and into deionized water and and pH thereof was measured. The value of $\Delta pH$ were determined as in Example IV and are tabulated below. A pH meter having a flat surface electrode obtained from Markson Science, Inc. (No. 1207 BactiMedia combination pH/reference electrode) was used for these measurements.

| pH of Poly-electrolyte Solution Aliquots | $\Delta$ pH Values Produced by Urines of Indicated Specific Gravities | | |
|---|---|---|---|
| | Sp. Gr. 1.005 | Sp. Gr. 1.015 | Sp. Gr. 1.030 |
| 4.0 | 0.11 | 0.05 | 0.00 |
| 5.0 | 0.5 | 0.64 | 0.70 |
| 6.0 | 0.56 | 0.88 | 1.09 |
| 7.0 | 0.76 | 1.29 | 1.68 |
| 7.5 | 0.91 | 1.40 | 1.98 |
| 8.0 | 1.15 | 1.73 | 2.29 |
| 8.25 | 1.10 | 1.82 | 2.10 |

Figure 5:
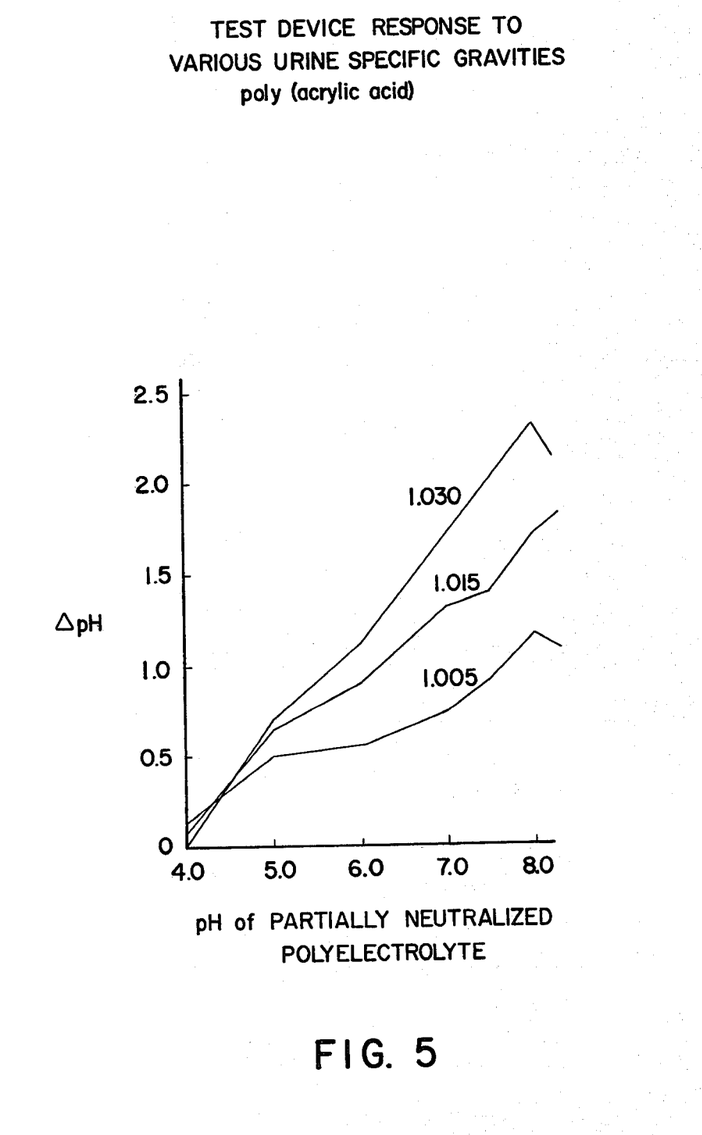

The data in the above table is plotted in FIG. 5, which, like FIG. 4, shows that the degree of separation of the curves therein increases markedly as the degree of neutralization, i.e., the pH, of the polyelectrolyte increases.

Example IV—Performance of Poly(vinylamine) in a Carrier Matrix

The polyelectrolyte employed in Example III was further studied to observe its behavior in measuring various urine specific gravities when incorporated with a carrier matrix.

Test devices were prepared and tested as in Examples IV and V except that poly(vinylamine) was substituted for Gantrez S-97 and poly(acrylic acid), respectively. A solution was prepared comprising 20 grams of poly(vinylamine) (obtained from Dynapol, Inc. 60,000 M.W., see Dawson et al., J.A.C.S. 98, 5996, 1976) per liter of deionized water. The polyelectrolyte used was in the hydrochloride form and thus was in the completely neutralized state. Aliquots of this solution were respectively titrated with 1.0 N NaOH to produce the solution pH levels stated in the table below. Strips of filter paper obtained from Eaton and Dikeman (No. 204) were respectively dipped into these aliquots and dried. They were then respectively dipped into different known specific gravity urines and into deionized water and the pH thereof was measured using the flat surface electrode described in Examples IV and V. The values of ΔpH were then determined as in Examples IV and V and are tabulated below.

| pH of Poly-electrolyte Solution Aliquots | Δ pH Values Produced by Urines of Indicated Specific Gravities | | |
|---|---|---|---|
| | Sp. Gr. 1.005 | Sp. Gr. 1.015 | Sp. Gr. 1.030 |
| 2.8 | 1.05 | 1.60 | 1.78 |
| 3.0 | 1.06 | 1.64 | 1.92 |
| 3.5 | .89 | 1.11 | 1.29 |
| 4.0 | .89 | 1.17 | 1.21 |
| 6.0 | +.06 | −.10 | −.33 |
| 8.0 | −0.71 | −.99 | −1.70 |
| 10.0 | −1.45 | −1.47 | −2.24 |
| 11.0 | −1.80 | −2.50 | −2.81 |
| 12.0 | −2.24 | −2.57 | −3.07 |

Figure 6:
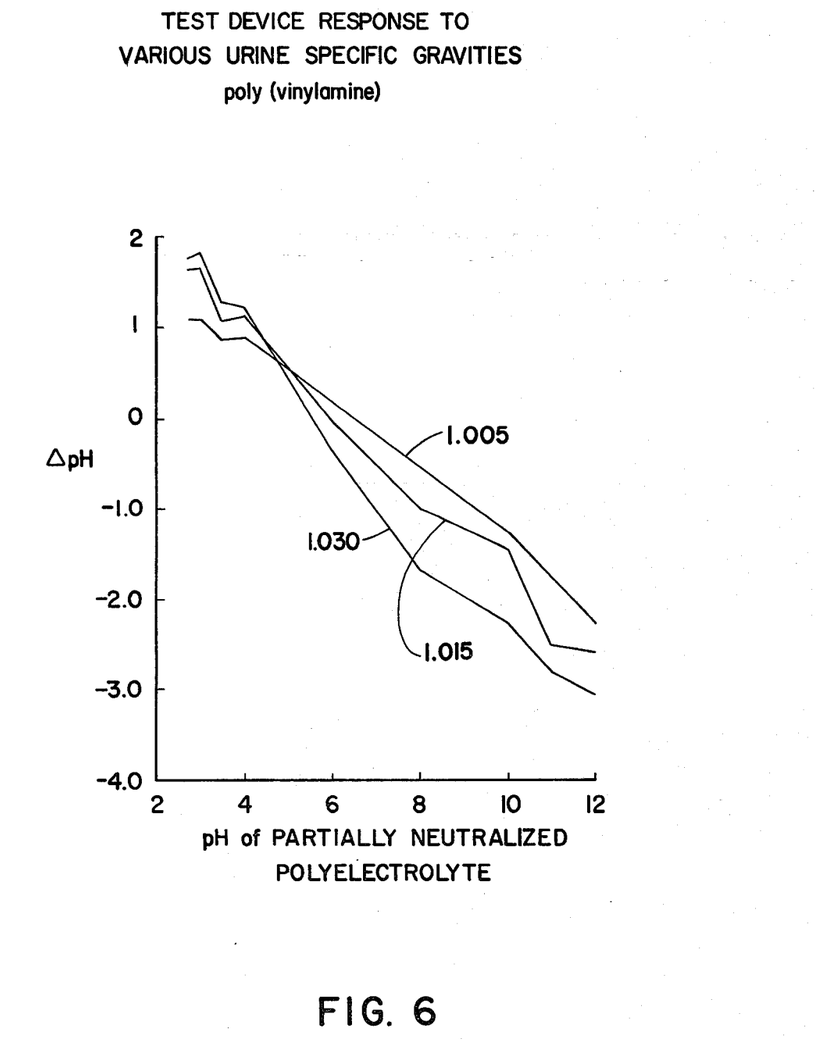

The graph of this data, FIG. 6, portrays useful separation when the polyelectrolyte is partially neutralized to below about pH 5. Thus the curve for urine having a specific gravity of 1.005 results in a much smaller change in pH than for urine at a specific gravity of 1.030. The urine having a specific gravity of 1.015 resulted in intermediate ΔpH values as expected.

This effect is even more dramatically demonstrated when the poly(vinylamine) test devices are respectively dipped into aqueous salt solutions of different ionic strengths and into deionized water and the pH thereof measured to provide ΔpH values. Thus strips prepared as above were tested with various concentrations of sodium chloride in deionized water. Specifically these salt solution concentrations were 0.5, 1.5 and 3.0 N in NaCl. The data obtained in this experiment is tabulated below and plotted in FIG. 7. Curves A, B and C correspond to salt solutions of 3.0, 1.5 and 0.5 N in NaCl, respectively.

| pH of Poly-electrolyte Solution Aliquots | Δ pH Values Produced by Urines of Indicated Specific Gravities | | |
|---|---|---|---|
| | 0.5N NaCl | 1.5N NaCl | 3.0N NaCl |
| 2.8 | .60 | .63 | .93 |
| 3.0 | 1.04 | 1.37 | 1.46 |
| 3.5 | .88 | .99 | 1.23 |
| 4.0 | 1.00 | 1.32 | 1.61 |
| 6.0 | .90 | .93 | 1.03 |
| 8.0 | .64 | .64 | .68 |
| 10.0 | .61 | .64 | .60 |
| 11.0 | −.01 | −.03 | −.10 |
| 12.0 | −.09 | −.22 | −.29 |

Figure 7:
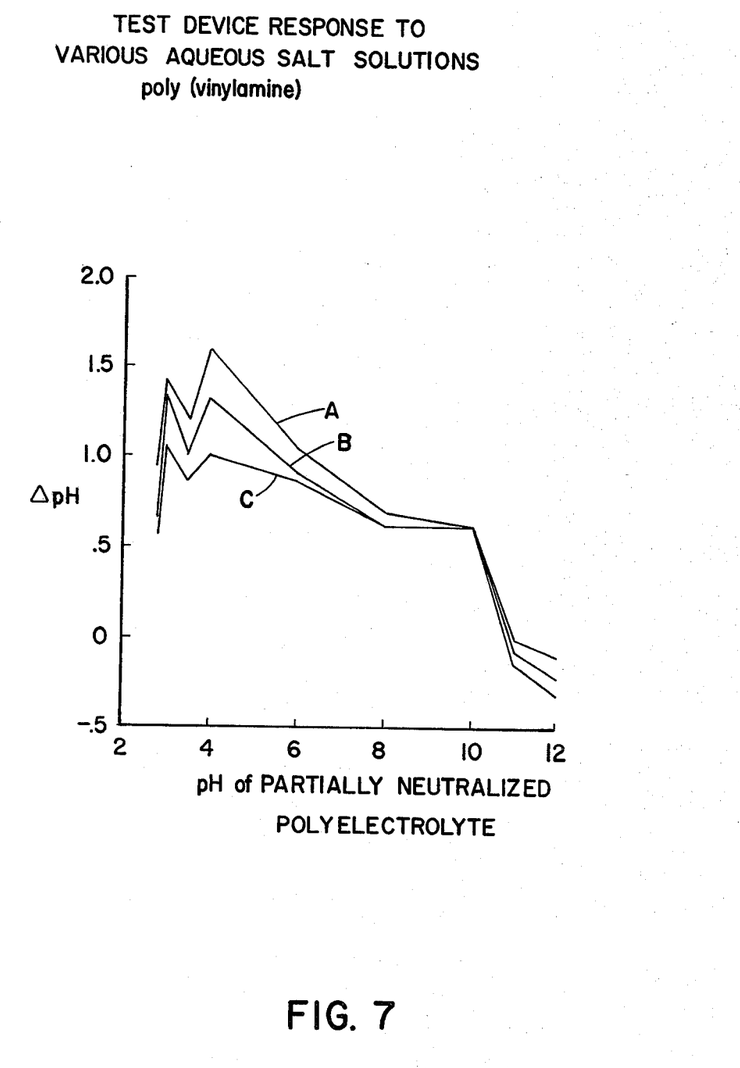
FIG. 7 shows similar performance of poly(vinylamine) in aqueous salt solutions of varying concentrations. Finally.

Referring to FIG. 7, at pH 10 where the polyelectrolyte is essentially unprotonated and uncharged, the effect of varying salt concentration is virtually nonexistent. Partial neutralization of the polymer, however, effects a steadily increasing divergence of performance in response to ionic strength, as evidenced by the increasing difference between the respective plots reflecting widely divergent ΔpH response to differing ionic strengths.

Example VII—Test Device Prepared Using Maleic Anhydride/Methylvinylether Copolymer and Bromothymol Blue The test composition of Example I was employed in a carrier matrix together with bromothymol blue, a known pH indicator, to dtudy the characteristics of the present invention with respect to visual determination of specific gravity.

A solution was prepared containing 20 grams of Gantrez S-97 per liter of deionized water. An aliquot of this solution was titrated with NaOH until the resultant solution pH was 8.0 as measured with the pH meter and electrode described in Example I. A strip of filter paper (Eaton & Dikeman No. 204) was immersed in the partially titrated (neutralized) aliquot and subsequently dried. The dried polymer-bearing strip was then immersed in a methanol solution of bromothymol blue at a concentration of 1.2 grams per liter. After drying, the filter paper strip was mounted on a clear plastic backing material (Trycite, obtained from Dow Chemical Co.) using double faced adhesive tape (Double Stick, obtained from 3M Company). The resultant test devices each comprised a strip of Trycite measuring about 3.5 in. by 0.2 in., one end of which bore a square of the impregnated filter paper measuring 0.2 in. on a side. The rest of the Trycite served as a handle.

The sensitivity of these test devices to specific gravity was studied by testing with three different specific gravity urine samples and with water. A device was immersed in the particular test solution and quickly removed. After 60 seconds the device was examined in reflectance spectrophotometer which scans and measures the intensity of reflected light from the test device over the visible spectral regions every half a second.

Figure 8:
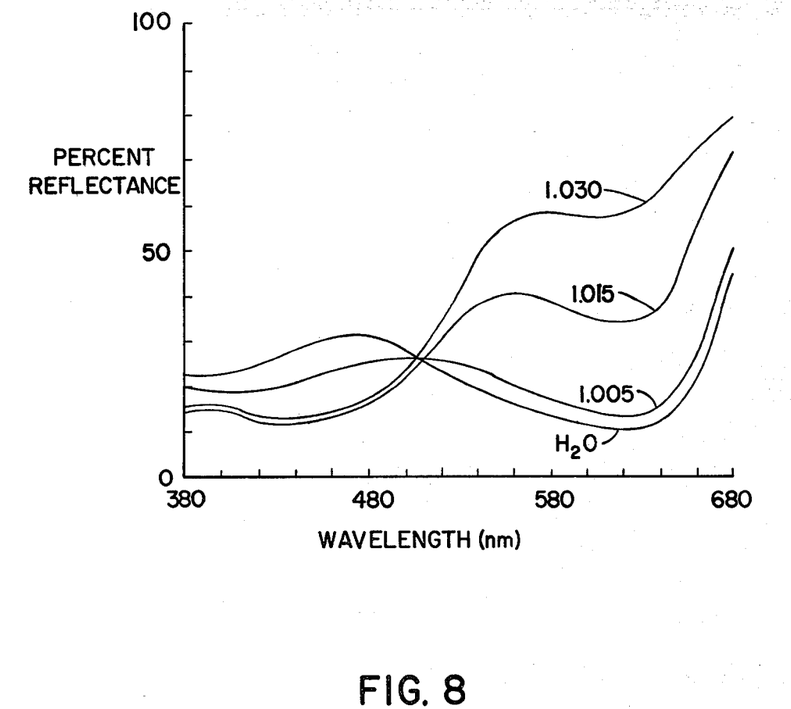
FIG. 8 shows the performance of a preferred device.

The data obtained at 60 seconds is plotted in FIG. 8 and shows marked separation enabling easy and accurate specific gravity differentiation between water (specific gravity 1.000) and urines at specific gravity levels of 1.005, 1.015 and 1.030. Visual color differentiation was equally easy, the device exhibiting a blue color with water, blue-green with urine at specific gravity 1.005, green at 1.015 and yellow at 1.030.

This example demonstrates the relationship between partial polyelectrolyte neutralization and specific gravity or ionic strength determination. The Gantrez solution from which the device was made had a pH of about 8. Referring to curve A of FIG. 1, this pH corresponds to about 6.8 ml of titrant. Using the calculation described in Example I, this corresponds to about 79% neutralization. The remarkable differentiation between specific gravity levels realized in the foregoing experiment is attributable to this relatively high degree of polyelectrolyte neutralization.

What is claimed is:

1. A test means for determining the ionic strength or specific gravity of an aqueous test sample, said test means comprising a weakly acidic or weakly basic polyelectrolyte polymer, said polymer being at least about 50 percent neutralized, and indicator means capable of producing a detectable response to ion exchange between said polyelectrolyte and said sample.

2. The test means of claim 1 in which said polymer is a weakly acidic polyelectrolyte.

3. The test means of claim 1 in which said polymer is a weakly basic polyelectrolyte.

4. The test means of claim 1 in which said polyelectrolyte is poly(acrylic acid), poly(maleic acid), maleic acidvinylmethyl ether copolymer, poly(methacrylic acid), styrenemaleic acid copolymer, poly(vinylamine), or poly(4-vinylpyridine).

5. The test means of any one of claims 1-4 in which said polyelectrolyte polymer is about 75 to about 95 percent neutralized.

6. The test means of any one of claims 1-4 in which said indicator means is a pH indicator substance.

7. The test means of any one of claims 1-4 in which said indicator means is a pH indicator substance, and said polyelectrolyte polymer is about 75 to about 95 percent neutralized.

8. The test means of claim 1 in which said polyelectrolyte is a methylvinylether-maleic acid copolymer, and in which said indicator means is bromothymol blue.

9. A test device for determining the ionic strength or specific gravity of an aqueous test sample, said device comprising a carrier matrix incorporated with the test means of any of claims 1-4 or 8.

10. A test device for determining the ionic strength or specific gravity of an aqueous test sample, said device comprising a carrier matrix incorporated with the test means of claim 5.

11. A test device for determining the ionic strength or specific gravity of an aqueous test sample, said device comprising a carrier matrix incorporated with the test means of claim 6.

12. A test device for determining the ionic strength of specific gravity of an aqueous test sample, said device comprising a carrier matrix incorporated with the test means of claim 7.

13. A method for determining the ionic strength or specific gravity of an aqueous test sample, said method comprising contacting said sample with the test means of any of claims 1-4 or 8 and observing a detectable response.

14. A method for determining the ionic strength or specific gravity of an aqueous test sample, said method comprising contacting said sample with the test means of claim 5 and observing a detectable response.

15. A method for determining the ionic strength or specific gravity of an aqueous test sample, said method comprising contacting said sample with the test means of claim 6 and observing a detectable response.

16. A method for determining the ionic strength or specific gravity of an aqueous test sample, said method comprising contacting said sample with the test means of claim 7 and observing a detectable response.

17. A method for determining the ionic strength or specific gravity of an aqueous test sample, said method comprising contacting said sample with the device of claim 9 and observing a detectable response.

18. A method for determining the ionic strength or specific gravity of an aqueous test sample, said method comprising contacting said sample with the device of claim 10 and observing a detectable response.

19. A method for determining the ionic strength or specific gravity of an aqueous test sample, said method comprising contacting said sample with the device of claim 11 and observing a detectable response.

20. A method of determining the ionic strength or specific gravity of an aqueous test sample, said method comprising contacting said sample with the device of claim 12 and observing a detectable response.

21. A method for preparing a test device for determining the ionic strength or specific gravity of an aqueous test sample, said method comprising the steps of
neutralizing at least 50 percent of the ionizable groups of a weakly acidic or weakly basic polyelectolyte polymer, and
incorporating said polymer and a pH indicator with a carrier matrix.

22. The method of claim 21 wherein said polyelectrolyte polymer is about 75 to about 95 percent neutralized.

23. The method of claims 21 or 22 wherein said polymer and said pH indicator are incorporated with said matrix by combination thereof with a suitable solvent to form an impregnation mixture, and said carrier matrix is contacted with said mixture and dried.

24. A method for preparing a test device for determining the ionic strength or specific gravity of an aqueous test sample, said method comprising the steps of
preparing an aqueous solution of a copolymer of maleic acid and methylvinylether,
adding an aqueous solution of a base to said copolymer solution sufficient to neutralize at least 50 percent of the acid groups of said copolymer.
contacting a carrier matrix with the partly neutralized polymer solution thereby incorporating said polymer with said matrix,
drying the polymer-incorporated matrix, and
incorporating a pH indicator with said dried matrix.

25. The method of claim 24 wherein said pH indicator is bromothymol blue and said indicator is incorporated with said dried polymer-incorporated matrix by preparing a solution of said indicator in methanol, and contacting said polymer-incorporated matrix with said indicator solution.

* * * * *